United States Patent [19]

Kunz et al.

[11] Patent Number: 4,491,759
[45] Date of Patent: Jan. 1, 1985

[54] PIEZOELECTRIC VIBRATION EXCITER, ESPECIALLY FOR DESTRUCTIVE MATERIAL TESTING

[75] Inventors: Werner Kunz, Munich; Walter Voigt, Rain, both of Fed. Rep. of Germany

[73] Assignee: MTU Motoren-und Turbinen-Union Muenchen GmbH, Munich, Fed. Rep. of Germany

[21] Appl. No.: 582,252

[22] Filed: Feb. 22, 1984

[30] Foreign Application Priority Data

Mar. 14, 1983 [DE] Fed. Rep. of Germany ....... 3309068

[51] Int. Cl.³ .............................................. H01L 41/08
[52] U.S. Cl. ..................................... 310/328; 73/808; 73/860; 310/323; 310/334
[58] Field of Search ............... 310/322, 323, 328, 334, 310/335; 73/577, 579, 595, 763, 783, 788, 799, 808, 810, 811, 855, 856, 860

[56] References Cited

U.S. PATENT DOCUMENTS

| | | | |
|---|---|---|---|
| 1,930,905 | 10/1933 | Nicolson | 310/323 |
| 2,936,612 | 5/1960 | Mason | 73/808 X |
| 3,563,086 | 2/1971 | Reed, Jr. | 73/860 X |
| 3,710,150 | 1/1973 | McMaster | 310/323 |
| 4,233,849 | 11/1980 | Defebvre | |

FOREIGN PATENT DOCUMENTS 2544140 4/1976 Fed. Rep. of Germany .
2939923 10/1979 Fed. Rep. of Germany .

*Primary Examiner*—Mark O. Budd
*Attorney, Agent, or Firm*—W. G. Fasse; D. H. Kane, Jr.

[57] ABSTRACT

A piezoelectric vibration exciter for generating mechanical vibrations for the purpose of destructive material or specimen testing has two equally sized disk stacks, each with an even number of piezoceramic disks. A vibration armature serving as a clamping device for the test specimen is arranged between the two disk stacks in a stiff clamping frame having a bail and a base plate. The assembly containing the disk stacks and the vibration armature is clamped in position in the stiff clamping frame. The piezoceramic disks are energized with an AC voltage so that one disk stack will axially contract in phase with the voltage, while the other disk stack will axially expand. As a result, the vibration armature and the test specimen arranged between the disks reciprocate at the frequency of the AC voltage input.

9 Claims, 1 Drawing Figure

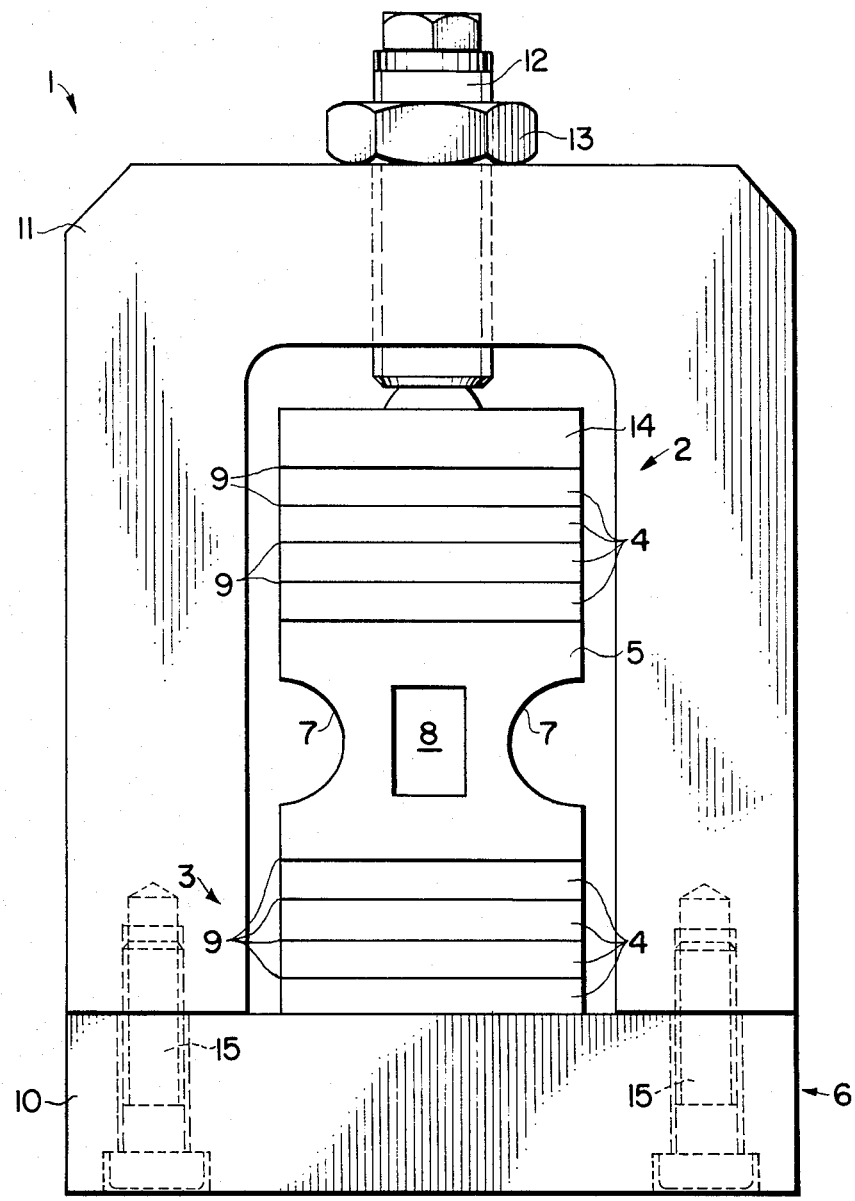

PIEZOELECTRIC VIBRATION EXCITER, ESPECIALLY FOR DESTRUCTIVE MATERIAL TESTING

FIELD OF THE INVENTION

The invention relates to a piezoelectric vibration exciter for generating mechanical vibrations for the purpose of destructive material testing on component test specimens. Such exciter comprises piezoceramic disks mechanically connected to a test specimen. These disks are operationally energized or excited with an AC voltage applied to the disks.

DESCRIPTION OF THE PRIOR ART

Commercially available piezoelectric vibration exciters normally operate on the principle of a heavily damped spring mass system in which piezoceramic rings or disks are arranged as a stack between two masses and clamped together by one or several tie bolts acting as springs. When one tie bolt is used it normally passes through the stack. When several tie bolts as shown in German Patent Publication No. 2,939,923 are used, such bolts are arranged around the outside of the stack. The disks are metallized on their faces. When an AC voltage is applied, the disks change in thickness against the force of the spring in rythmic synchronism with the voltage alternations. The resonant frequencies of the vibration system vary with the magnitude of the masses used, with the spring constant and the thermal response of the tie bolt or bolts and with the weight of the test specimen.

An accurate tuning to the intended test frequency of the test specimen connected to the testing device is required for achieving maximum vibration amplitudes. This tuning produces considerable non-linearities of the frequency response curves that can be leveled off only by considerable damping, which in turn will transform a large portion of the power input into heat loss whereby the vibration amplitudes remain rather small. Besides, the conventional vibration exciter disadvantageously generates an undesirably large quantity of heat in the system.

OBJECTS OF THE INVENTION

In view of the above it is the aim of the invention to achieve the following objects singly or in combination:

to provide a piezoelectric vibration exciter for generating mechanical vibrations for destructive material testing which is simple in construction, yet avoids the disadvantages of the prior art;

to construct a piezoelectric vibration generator which permits a continuous tuning over a wide 20 kHz to 100 kHz frequency range with a largely linear frequency response;

to provide a piezoelectric vibration generator which, due to moderate damping of the vibrating parts, has an improved efficiency between its electrical input energy and its kinetic output energy;

to provide a piezoelectric testing apparatus especially suitable for fatigue testing of high pressure compressor blades; and to minimize energy losses in the form of heat losses of the applied energy for exciting the piezoelectric vibration generator.

SUMMARY OF THE INVENTION

According to the present invention a vibration armature, in the form of a clamping device for the test specimen, is arranged between two equally large piezoceramic disk stacks, wherein the disk stacks are clamped in position in a stiff clamping frame, wherein each stack contains the same even number of piezoceramic disks which are wired so that one disk stack will axially contract in phase with an applied AC voltage, while the other disk stack will axially expand also in phase with the applied voltage, or in synchronism therewith.

The vibration armature preferably is a lightweight component having at least one lateral notch and particularly having a central through-hole for accommodating a test specimen in a snug fit. Such test specimen may, for example be a high-pressure compressor blade of a gas turbine held in place by a location fit.

The vibration armature is suitably formed symmetrically about the central axis of vibration of the exciting system and has the size of the adjacent piezoceramic disks, which preferably have a circular shape. Each disk stack preferably comprises four piezoceramic disks and metal contact sheets are arranged between adjacent disks of a stack.

The clamping frame of the vibration exciter essentially comprises a base plate and a clamping bail bolted to one another. A clamping spindle is located centrally in the clamping bail which can be secured with a counternut on the side remote from the base plate. The assembly comprising the two disk stacks and the vibration armature between the stacks can suitably be clamped in position inside the bail by means of the clamping spindle acting through a pressure plate.

BRIEF FIGURE DESCRIPTION

In order that the invention may be clearly understood, it will now be described, by way of example, with reference to the single figure of the accompanying drawing illustrating a front elevational view of a piezoelectric vibration generator.

DETAILED DESCRIPTION OF PREFERRED EXAMPLE EMBODIMENTS AND OF THE BEST MODE OF THE INVENTION

The drawing shows a schematic front view of a continuously tunable, high-efficiency piezoelectric vibration exciter 1 for generating mechanical vibrations for the purpose of destructive material testing of components in a frequency range from 20 kHz to 100 kHz.

The vibration exciter 1 has two piezoceramic disk stacks 2, 3 and a lightweight vibration armature 5 located between the stacks, which are arranged in a stiff clamping frame 6.

The vibration armature 5 is arranged in the immediate vicinity of and in mechanical contact with the two piezoelectric disk stacks 2 and 3, and forms a clamping device for a test specimen not shown. A central through-hole 8 is provided in the vibration armature to accommodate the test specimen in a snug fit. One or more circumferential or rather outwardly located indentations 7 are recessed into the armature to reduce its weight. The hole 8 and the indentations are formed by a machining operation.

Each of the two disk stacks 2 and 3 comprises an even number of piezoceramic disks 4. Each stack has the same number of disks, for example four disks in each stack. On the face each of the disks has a metallic contact sheet 9 to operationally produce the piezoelectric effect. These sheets are wired so that when an AC voltage is applied, one of the stacks will axially contract in phase with the voltage, while the other stack will expand and vice versa. In the operation the vibration armature 5 arranged between the stacks 2, 3 reciprocates at the frequency of the AC voltage applied, and thus the test specimen connected to the vibration armature 5 also vibrates.

The assembly comprising the two disk stacks 2 and 3 and the vibration armature 5 between them is clamped in position in a stiff clamping frame 6 essentially comprising a flat base plate 10 and a channel-section clamping bail 11 bolted to it at 15. The bail 11 has, for example, a U-configuration as shown with two spaced side legs and an upper cross bar interconnecting the side legs. On its side pointing away from the base plate 10 the clamping bail has a central threaded hole to receive a threaded clamping spindle 12. The assembly containing the disk stacks 2, 3 and the vibration armature 5 is accommodated in the space between the side legs of the clamping bail 11 and is tensioned by the clamping spindle 12 acting through an upper pressure plate 14. A counternut 13 on the clamping spindle 12, when tightened, serves to maintain the tension.

In operation the specimen to be tested for its fatigue characteristics, e.g., a high-pressure compressor blade of a gas turbine, is snugly received and suitably secured in the hole 8 of the armature 5 in the clamping device. An AC voltage in a wide frequency range of 20 kHz to 100 kHz is then applied to the system. The amplitudes of vibration set up in the piezoceramic disks 2, 3 are transferred to the mechanically connected vibration armature 5, which reciprocates at the frequency of the AC voltage input to move the test specimen accordingly. The system of the present invention permits continuous tuning over a wide frequency range with a largely linear frequency response. Hence, the mechanical damping of the vibrating parts remains moderate.

The heat loss of the power input is minimal, whereby comparatively large vibration amplitudes are achieved. Hence, the vibration exciting system of the present invention has a good efficiency. By increasing the number of disks in the stacks it is possible to increase the vibration amplitudes without changing the AC voltage input. However, it is necessary that the stacks have the same size and, for wiring reasons, there must be an even number of disks in each stack. A further advantage is provided in that, within certain limits, the weight of the test specimen has no effect on the vibration amplitudes to be achieved. This is so because the vibration armature 5 is moved by an enforced vibration rather than by a resonant system vibration. This is contrary to the known piezoelectric vibration exciter, which operates on the principle of a heavily damped spring mass system as mentioned above.

Fundamental difference between the prior art devices and the inventive arrangement depends on the simultaneous action of two disc stacks under different polarity according to the invention.

Although the invention has been described with reference to specific example embodiments, it will be appreciated, that it is intended to cover all modifications and equivalents within the scope of the appended claims.

What is claimed is:

1. A piezoelectric vibration exciter apparatus for generating mechanical vibrations for material testing, comprising a first stack of an even number of piezoceramic disks, a second stack of piezoceramic disks corresponding in number to said even number of disks in said first stack, each stack having the same size, vibration armature means for holding a test specimen operatively mounted between said first and second stacks, stiff mounting means for clamping said two stacks and said vibration armature means in said stiff mounting means, and means for applying an energizing voltage to each piezoelectric disk in each stack in such a manner that upon application of an alternating voltage to said disks one stack contracts axially in phase or synchronism with the applied alternating voltage while the other stack expands axially and vice versa.

2. The apparatus of claim 1, wherein said vibration armature means (5) comprises a substantially centrally located throughgoing hole (8) for holding a specimen to be tested in a location fit manner.

3. The apparatus of claim 1, wherein said vibration armature means (5) comprise lateral indentations (7) forming approximately an I-configuration whereby the weight of the vibration armature means is reduced.

4. The apparatus of claim 3, wherein said vibration armature means (5) comprises a substantially centrally located throughgoing hole (8) for holding a specimen to be tested in a location fit manner, said through-going hole (8) being located centrally between said indentations (7).

5. The apparatus of claim 1, wherein said stacks have a central vibration axis, said vibration armature means having a configuration which is centrally symmetric relative to said central vibration axis.

6. The apparatus of claim 1, wherein said disks in each stack are circular and have the same diameter, said vibration armature means also being circular in cross-section and having the same diameter as said disks.

7. The apparatus of claim 1, wherein each stack comprises four piezoceramic disks, said energizing voltage applying means comprising metal foils covering one surface of each disk in each stack.

8. The apparatus of claim 1, wherein said stiff mounting means comprise a base plate, a clamping bail, means rigidly securing said clamping bail to said base plate, a threaded hole centrally in said clamping bail opposite said base plate, a clamping spindle extending through said threaded hole, and a jam nut on said clamping spindle for arresting said clamping spindle in a clamping position.

9. The apparatus of claim 8, further comprising a pressure plate at an inner free end of said clamping spindle for holding said first and second stacks with the vibration armature means between the stacks in place in said clamping bail.

* * * * *